United States Patent [19]
Prieto et al.

[11] Patent Number: 5,945,314
[45] Date of Patent: Aug. 31, 1999

[54] PROCESS FOR SYNTHESIZING OLIGOSACCHARIDES

[75] Inventors: Pedro A. Prieto, West Worthington; Karen M. Kleman-Leyer, Westerville, both of Ohio

[73] Assignee: Abbott Laboratories, Abbott Park, Ill.

[21] Appl. No.: 08/829,010

[22] Filed: Mar. 31, 1997

[51] Int. Cl.⁶ .............................. C12P 19/12; C12P 19/04
[52] U.S. Cl. ............................................ 435/101; 435/100
[58] Field of Search .................................... 435/100, 101, 435/105

[56] References Cited

U.S. PATENT DOCUMENTS

| | | | |
|---|---|---|---|
| 4,219,571 | 8/1980 | Miyake | 426/48 |
| 5,288,637 | 2/1994 | Roth | 435/288 |
| 5,516,665 | 5/1996 | Wong | 435/97 |
| 5,541,083 | 7/1996 | Paulson et al. | 435/41 |
| 5,583,042 | 12/1996 | Roth | 435/288.1 |
| 5,618,705 | 4/1997 | Laine et al. | 435/97 |
| 5,641,668 | 6/1997 | Berger et al. | 435/193 |
| 5,728,554 | 3/1998 | Bayer et al. | 435/97 |
| 5,776,772 | 7/1998 | Paulson et al. | 435/320.1 |

FOREIGN PATENT DOCUMENTS

| | | |
|---|---|---|
| 9116449 | 10/1991 | WIPO . |
| 9502683 | 1/1995 | WIPO . |
| 9610086 | 4/1996 | WIPO . |

OTHER PUBLICATIONS

J. Sambrook et al., *Molecular Cloning: A Laboratory Manual*, 2nd Edition, Cold Spring Harbor Laboratory Press (1989).

B.W. Petschow et al., "Growth Promotion of Bifidobacterium Species by Whey and Casein Fractions From Human and Bovine Milk", *Journal of Clinical Microbiology*, Feb., (1990), pp. 287–292.

H. Beerens et al., "Influence of Breast–Feeding on the Bifid Flora of the Newborn Intestine", *The American Journal of Clinical Nutrition*, vol. 33, (1980), pp. 2434–2439.

*Primary Examiner*—Bradley L. Sisson
*Assistant Examiner*—Einar Stole
*Attorney, Agent, or Firm*—Cheryl L. Becker

[57] ABSTRACT

The present invention relates to a process for synthesizing oligosaccharides. The process involves contacting an acceptor moiety with unpurified sugar-nucleotides and/or unpurified glycosyltransferase to synthesize oligosaccharides.

22 Claims, No Drawings

PROCESS FOR SYNTHESIZING OLIGOSACCHARIDES

CROSS REFERENCE TO RELATED APPLICATIONS

The present application is related to the U.S. patent applications entitled, "Nutritional Formulations Containing Lacto-N-neoTetraose," and "Nutritional Formulations Containing Oligosaccharides," all of which are filed concurrently herewith, and the texts of which are herein incorporated by reference.

TECHNICAL FIELD OF THE INVENTION

The present invention relates to a process for synthesizing oligosaccharide compositions. More specifically, the invention pertains to an economical method for synthesizing oligosaccharides using crude, unpurified sugar-nucleotides and/or glycosyltransferases.

BACKGROUND OF THE INVENTION

The term "carbohydrate" embraces a wide variety of chemical compounds having the general formula $(CH_2O)_n$ and encompasses such compounds as monosaccharides, disaccharides, oligosaccharides, polysaccharides and their aminated, sulfated, acetylated and other derivated forms (U.S. Pat. No. 5,288,637, this patent, as well as all other patents and publications disclosed herein are incorporated by reference). Oligosaccharides are chains composed of sugar units, which are also known as monosaccharides. Sugar units can be arranged in any order and linked by their sugar units in any number of different ways. Id. Therefore, the number of different stereoisomeric oligosaccharide chains possible is exceedingly large. Id.

Numerous classical chemical techniques for the synthesis of carbohydrates have been developed, but these techniques require selective protection and deprotection. Organic synthesis of oligosaccharides is further hampered by the lability of many glycosidic bonds, difficulties in achieving regioselective sugar coupling, and generally low synthetic yields. Therefore, unlike peptide synthesis, traditional synthetic organic chemistry cannot provide for quantitative, reliable synthesis of even fairly simple oligosaccharides.

Recent advances in oligosaccharide synthesis have occurred with the characterization, cloning and isolation of glycosyltransferases. These enzymes can be used in vitro to prepare oligosaccharides, polysaccharides and other glycoconjugates. The advantage of biosynthesis with glycosyltransferases is that the glycosidic linkages formed by enzymes are highly stereo and regiospecific. Each enzyme catalyzes the linkage of specific sugar residues to other specific acceptor moieties, such as an oligosaccharide, lipid or protein. For example, U.S. Pat. No. 5,288,637 discloses the stoichiometric synthesis of oligosaccharides using acceptor moieties, purified sugar-nucleotides and glycosyltransferases. The problem with this process, however, is that it is not commercially feasible due to the extremely high cost of the purified sugar-nucleotides. Therefore, a need exists for an economical process of synthesizing oligosaccharides using sugar-nucleotides and glycosyltransferases.

SUMMARY OF THE INVENTION

The present invention relates to a process for synthesizing oligosaccharides in vitro. The process involves adding an acceptor moiety and a catalytic amount of a glycosyltransferase to a microorganism culture that produces a sugar-nucleotide or combinations of sugar-nucleotides and nucleotides. The mixture is maintained under conditions and for a period of time sufficient for oligosaccharide formation. Alternatively, the present invention also involves a process for synthesizing oligosaccharides by adding an acceptor moiety and intact host cells transformed with a polynucleotide that encodes a catalytic amount of a glycosyltransferase to sugar-nucleotides having a sugar unit to form a mixture and maintaining the mixture under conditions and for a period of time sufficient for oligosaccharide formation.

DETAILED DESCRIPTION OF THE INVENTION

The present invention relates to a process for synthesizing oligosaccharides in vitro. The process involves adding an acceptor molecule and a glycosyltransferase to sugar-nucleotides under conditions and time sufficient to allow for oligosaccharide formation. The sugar-nucleotide and/or the glycosyltransferase used in the process of this invention are present in a crude, unpurified form. The use of the unpurified sugar-nucleotide and/or the unpurified glycosyltransferase makes the process of the present invention more economical than processes known and employed in the prior art that use purified sugar-nucleotides and purified or semipurified glycosyltransferases. (See U.S. Pat. No. 5,288,637). The process of the present invention is amenable for use in a single or multiple batch operation, and the oligosaccharides produced, according to the process of the present invention, may be synthesized in a single or in multiple reaction vessels.

As known in the art, a monosaccharide is a sugar molecule that contains one sugar unit. As used herein, the term "sugar unit" means a monosaccharide. As also known in the art, a disaccharide is a sugar molecule that contains 2 sugar units, a trisaccharide is a sugar molecule that contains 3 sugar units, an oligosaccharide is a sugar molecule that contains between 2–10 sugar units, and a polysaccharide is a sugar molecule that contains greater than 10 sugar units. The sugar units in a di-, tri- and oligosaccharide are all connected by glycosidic linkages. Nonetheless, as used in the present invention, the term "oligosaccharide" means a sugar molecule that contains at least two sugar units.

The acceptor moiety employed in the present invention can be any molecule that is capable of being covalently bound to a sugar unit. Suitable acceptor moieties that can be used in this invention include, for example, proteins, glycoproteins, lipids, glycolipids, carbohydrates or any molecule having a sugar unit contained in its structure. The preferred acceptor moiety is a carbohydrate. The most preferred acceptor moiety is a mono-, di-, tri, or oligosaccharide. When the acceptor moiety is terminated by a sugar unit, subsequent sugar units added to the molecule will typically be covalently bound to the nonreducing terminus of the end sugar of the molecule.

The sugar unit to be transferred to the acceptor moiety is provided by a sugar-nucleotide. In mammals, sugar-nucleotides are the building blocks for most oligosaccharides. Sugar-nucleotides are considered to be donor molecules since they provide sugar units to acceptor moieties during oligosaccharide synthesis. The sugar-nucleotides that may be used in the process of the present invention include, for example, saccharide terminated uridine mono- or di-phosphates, saccharide terminated guanosine mono- or di-phosphates and saccharide terminated cytidine mono- or di-phosphates. Examples of sugar-nucleotides that can be used in this invention include UDP-Glucose (UDP-Glc), UDP-N-acetylglucosamine (UDP-GlcNAc), UDP-Galactose (UDP-Gal), UDP-N-acetylgalactosamine (UDP-GalNAc), GDP-Mannose (GDP-Man), GDP-Fucose (GDP-Fuc) and CMP-N-acetylneuraminic acid (CMP-NeuAc).

Purified, semi-purified or unpurified sugar-nucleotides can be used in the present invention. As used herein, the term "purified and semi-purified sugar-nucleotides" refers to sugar nucleotides that have been processed in some manner, such as by ion-exchange chromatography or ultrafiltration, to increase their concentration and to separate the sugar-nucleotides from any other chemical compounds produced during the synthesis of said sugar-nucleotides. A dried, purified sugar nucleotide preparation is a preparation in which at least about 80% of the preparation's total weight is sugar nucleotides and no more than about 95% of the total weight of the preparation is sugar-nucleotides, counter-ions and water. For example, purified sugar nucleotides can be obtained by removing sugar nucleotides in a solution by precipitation, and then filtering the solution and then applying the solution to a selective ion exchange chromatography. The resulting solution is then lyophilized, or in the alternative, lyophilized and subjected to evaporation from ethanol or methanol to obtain purified sugar-nucleotides.

The term "semi-purified" as used herein refers to a sugar-nucleotide preparation where the actual residual content of the sugar-nucleotides in the preparation does not exceed 80% of the weight of the preparation. For example, semi-purified sugar nucleotides can be obtained by filtering a yeast solution containing sugar-nucleotides through a 10,000 M W filter and then drying the filtrate.

The term "unpurified" as used herein refers to sugar-nucleotides have not been processed in any manner, such as by ion-exchange chromatography or affinity chromatography, to increase their concentration and to separate the sugar-nucleotides from any chemical compounds produced during the biological or chemical synthesis of said sugar-nucleotides.

Sugar-nucleotides can be purified using any technique known in the art, such as by ion-exchange chromatography and ultrafiltration. See Smith, D., et al. Purified sugar-nucleotides are well known in the art and have frequently been employed in oligosaccharide synthesis. (Blake, D., et al., *Meth. Enzy.* 83 (1982) 127; Smith, D. F., *Meth. Enzy.* 83 (1982) 241).

Additionally, sugar-nucleotides produced by a microorganism culture can also be used in the present invention. The microorganism culture produces the sugar-nucleotides in a crude, unpurified form. Preferably, the sugar-nucleotides used in the process of this invention are in unpurified form and produced by a culture of microorganisms or by permeabilized or previously dried microorganisms.

The production of sugar-nucleotides using microorganisms, particularly yeast, is well known in the art (See Tochikura, T., et al., *J. Ferment. Technol.*, Vol. 46, No,. 12, p. 957–969 (1968) and Tochikura, T. et al., *Agr. Biol. Chem.*, Vol. 35, No. 2, p. 163–176 (1971)). Generally, the microorganism culture can be prepared by incubating sugars at room temperature or in a refrigerator with microorganisms and nucleotides or nucleotide precursors such as uridine mono- or di-phosphate, guanosine mono- or di-phosphate, or cytidine mono- or di- phosphate, orotate, in the presence of a phosphate source (such as phosphate or buffer), an energy source (such as glucose, fructose or maltose) and magnesium ions, for a sufficient amount of time to allow the microorganism to begin producing sugar-nucleotides. As used herein, the term "nucleotide precursor" refers to molecules that are used as intermediates in the synthesis of nucleotides via metabolic pathways, such as, nucleotides, purines or pyrimidines. Examples of sugar nucleotide precursors are uridine, orotate, citidine, adenosine, inosine, guanine, guanidine, guanosine, uridine, uridine mono-, di-, and tri-phosphates, citidine mono-, di- and tri-phosphates, guanosine mono-, di- and tri-phosphates. Precursors of purine synthesis, such as UMP and of UDP-sugar nucleotides, are: carbamoyl phosphate, aspartate, N-carbamoylaspartate, Dihydroorotate and orotidylate, other precursors are glycinamide ribonucleotide, formylglycinamide ribonucleotide, formylglycine ribonucleoitide, 5-aminonoimidazole ribonucleotide, 4-aminoimidazole-4crboxylate ribonucleotide 5-aminoimidazole-4-N-succinocarboxamide ribonucleotide, 5-aminoimidazole-4-carboxamideazole-4-carboxamide ribonucleotide, inosinate, adenylosuccinate, and xanthylate.

Any microorganism that is capable of producing sugar-nucleotides can be used in the present invention. For example, microorganisms of the genus Saccharomyces, Zygosaccharomyces, Torulopsis, Candida, Crypococcus, Brettanomyces, Mucor, Hansenula and Debaryomyces can be used. Examples of the strains of microorgansims that can be used to produce sugar-nucleotides are listed in Table 1.

Table 1

Saccharomyces
*S. cerevisiae*
   Baker's yeast (UDP-GlcNAc, UDP-Glc, GDP-Man)
   Brewer's yeast (UDP-GlcNAc, UDP-Glc, GDP-Man)
*S. fragilis* (UDP-Gal)
*S. lactis* (UDP-Glc, UDP-Gal)
*S. ludwigii* (UDP-GlcNAc)
Zygosaccharomyces
*Z. rouxii* (UDP-GlcNAc)
Torulopsis
*T. candida* (UDP-GlcNAc, UDP-Glc, UDP-Gal)
*T. spaerica* (UDP-Glc, UDP-Gal)
*T. xlinus* (GDP-Man)
*T. versatilis* (UDP-GlcNAc)
Candida
*C. famata* (UDP-GlcNac, UDP-Glc, UDP-Gal)
*C. intermedia* (UDP-Gal)
*C. krusei* (UDP-Glc)
*C. parapsilosus* (UDP-Glc)
*C. utilis* (GDP-Man)
*C. mycoderma* (UDP-Glc)
*C. pseudostopicalis* (UDP-Glc)
*C. tropicalis (UDP-GlcNAc)*
*Crypococcus albidus* (UDP-Glc)
Brettanomyces
*B. anomalus* (UDP-Glc, UDP-GlcNAc)
*B. clauseni* (UDP-Glc, UDP-Gal)
Mucor
*M. javanicus* (UDP-Glc)
*M. racemosus* (UDP-Glc)
*M. circinelloides* (UDP-Glc)
Hansenula
*H. jadinii* (GDP-Man)
*H. saturnus* (GDP-Man)
*H. suaveolens* (GDP-Man)
*H. capsulata* (UDP-Glc)

Debaryomyces

*D. subglobosus* (UDP-Glc, UDP-GlcNac)

*D. globosus* (UDP-GlcNac)

*D. cantavellii* (UDP-GlcNAc)

*D. japonicus* (UDP-GlcNAc)

*D. hansenii* (UDP-GlcNAc)

Preferably, the microorganisms used in this invention have been subjected to some type of processing such as drying, sonication, or solvent or detergent exposure. The preferred microorganism for use in this invention is *S. cerevisiae*, particularly, dried Baker's and dried Brewer's yeast, dried *Candida famata*, or *Zygosaccharomyces rouxii*.

In addition to the sugar-nucleotides, the microorganism culture or glycosyltransferase preparation may also contain one or more epimerases. An epimerse is an enzyme that changes the steroespecificity of hydroxyl groups at specific carbons in a saccharide. For example, an epimerase can be used to convert glucose to galactose and galactose to glucose. In the present invention, an epimerase may be used to convert UDP-Glc to UDP-Gal.

The crude, unpurified sugar-nucleotides described above are capable of providing component sugar units to an acceptor moiety when placed in contact with an acceptor moiety in the presence of at least one glycosyltransferase. As used herein, "glycosyltransferase" refers to an enzyme which facilitates the transfer of a sugar unit from one chemical entity (the donor molecule) to another (the acceptor moiety) and is named phenomenologically according to the sugar unit it transfers. For example, galactosyltransferases transfer galactose and fucosyltransferases transfer fucose. Glycosyltransferases that can be used in this invention include, for example, fucosyltransferases, sialyltransferases, N-acetylglucose-aminyltransferases, galactosyltransferases, N-acetylgalactosaminyltransferases, glucosyl-transferases and mannosyltransferases.

Glycosyltransferases are known to possess three domains which correspond to three different areas of the gene encoding the enzyme. The area of the gene found at the 3' end is known to encode the catalytically functionally domain (Lowe, *Seminars in Cell Biology*, (1991) 2:289–307). The glycosyltransferases used in the process of this invention contain at least this catalytic domain, but may contain up to the whole protein sequence.

The glycosyltransferases used in this invention can be obtained from any source and can be in purified or crude, unpurified form. As used herein, a "purified" glycosyltransferase refers to a glycosyltransferase that has been processed in some manner, such as by affinity chromatography, to increase the specific activity of the enzyme. The term "specific activity" refers to the units per milligram of protein. Methods for purifying glycosyltransferases are well known in the art. An "unpurified" glycosyltransferase as used herein refers to a glycosyltransferase that has not been processed in any manner, such as by affinity chromatography, to increase the specific activity of the enzyme. Preferably, the glycosyltransferases used in the process of the present invention are in unpurified form.

Genes encoding glycosyltransferases and methods for producing recombinant molecules expressing glycosyltransferases are well known in the art. For example, genes encoding glycosyltransferases from *Neisseria gonorrhoeae* and recombinant molecules expressing these genes are described in WO 96/10086 and U.S. Pat. No. 5,545,553.

Any gene encoding a glycosyltransferase can be inserted into a recombinant molecule. The polynucleotides constituting the gene may be obtained by standard procedures known in the art, such as from cloned DNA (such as a DNA "library"), chemical synthesis, cDNA cloning, or by the cloning of genomic DNA, or fragments thereof, from a desired cell as described in Sambrook, J., et al., Molecular Cloning A Laboratory Manual, 2d Edition, Cold Spring Harbor Laboratory Press (1989).

In the molecular cloning of the gene from genomic DNA, DNA fragments are generated, some of which will encode the desired gene. The DNA may then be cleaved at specific sites using various restriction enzymes. Alternatively, DNAse may be used in the presence of manganese to fragment the DNA, or the DNA can be physically sheared, as for example, by sonication. The linear DNA fragments can then be separated according to size by standard techniques, such as by agarose and polyacrylamide gel electrophoresis and column chromatography.

Once the DNA fragments are generated, identification of the specific DNA fragment containing the desired glycosyltransferase gene may be accomplished in a number of ways that are well known in the art, such as through nucleic acid hybridization with one or more labeled probes as described in Sambrook, J., et al., Molecular Cloning A Laboratory Manual, 2d Edition, Cold Spring Harbor Laboratory Press (1989). The presence of the desired gene may then be detected using assays based on the physical, chemical, or immunological properties of the expressed product.

Once the gene encoding a glycosyltransferase has been isolated, it can be inserted into an appropriate cloning vector. A large number of vector-host systems known in the art may be used. Possible vectors include, but are not limited to, plasmids or modified viruses, provided that the vector system is compatible with the host cell used. The vectors that can be used include, for example, an *E. coli* cloning vector, bacteriophages such as lambda derivatives, plasmids such as pBR322 derivatives or pUC plasmid derivatives.

The insertion of the gene into the cloning vector can be accomplished by any process known in the art such as by ligating the DNA fragment into a cloning vector that has complementary cohesive termini. Sambrook, J., et al., Molecular Cloning A Laboratory Manual, 2d Edition, Cold Spring Harbor Laboratory Press (1989). However, if the complementary restriction sites used to fragment the DNA are not present in the cloning vector, then the ends of the DNA molecules may have to be enzymatically modified. Alternatively, any site desired may be produced by ligating nucleotide "linker" sequences onto the DNA termini. These ligated linkers may comprise specific chemically synthesized oligonucleotides encoding restriction endonuclease recognition sequences. The cloning vector can be introduced into host cells via transformation, transfection, infection, electroporation, etc., so that many copies of the gene sequence are generated.

Transformation of host cells with a cloning vector that incorporates the glycosyltransferase gene enables the generation of multiple copies of the gene. Therefore, the gene may be obtained in large quantities by growing transformants, isolating the cloning vector from the transformants and, when needed, retrieving the inserted gene from the isolated cloning vector.

The cloning vector may contain genes encoding truncated forms of the enzyme (fragments) and derivatives of the gene that have the same functional activity as the full-length gene. A fragment or derivative is functionally active if it is capable of mediating transfer of a sugar unit to an acceptor moiety. For example, a cloning vector may contain a gene encoding the catalytically functional domain of a glycosyltransferase.

Once sufficient copies of the gene sequence have been generated, the gene encoding a glycosyltransferase, or a functionally active fragment or other derivative thereof, can be inserted into an appropriate recombinant molecule for use in the process of the present invention. The recombinant molecule is a polynucleotide expression vector that contains the necessary elements for the transcription and translation of the inserted protein-coding sequence. Preferably, the expression vector also includes an origin of replication. The necessary transcriptional and translation signals can also be supplied by the native glycosyltransferase gene and/or its flanking regions.

Once a recombinant molecule has been prepared, it is inserted into an acceptable host cell which will grow and divide to produce clones. A variety of host cell-vector systems may be utilized to express the gene. Suitable host cell-vector systems include, for example, bacterial expression systems, mammalian cell systems infected with a virus, such as a vaccinia virus or adenovirus, insect cell systems infected with a virus such as a baculovirus, microorganisms such as yeast containing yeast vectors, and bacteria transformed with bacteriophage DNA, plasmid DNA or cosmid DNA. The preferred host cell-vector system for use in this invention is a bacterial cell expression system. The most preferred host cells for use in this invention are *E. coli* cells.

Any of the methods previously described for the insertion of DNA fragments into a vector may be used to construct expression vectors containing a chimeric gene consisting of appropriate transcriptional/translation control signals and the protein coding sequences. Expression of the polynucleotide encoding an glycosyltransferase or peptide fragment thereof may be regulated by a second nucleic acid sequence so that the glycosyltransferase or peptide fragment is expressed in a host transformed with the recombinant DNA molecule. For example, expression of a glycosyltransferase may be controlled by any promoter/enhancer element known in the art, but these regulatory elements must be functional in the host selected for expression. For expression in bacteria, bacterial promoters are required. Promoters which may be used to control glycosyltransferase gene expression include, for example, the SV40 early promoter region, the promoter contained in the 3' long terminal repeat of Rous sarcoma virus, the herpes thymidine kinase promoter, the regulatory sequences of the metallothionein gene; prokaryotic expression vectors such as the β-lactamase promoter or the tac promoter.

Recombinant molecules containing the glycosyltransferase gene can be identified by PCR amplification of the desired plasmid DNA or specific mRNA, nucleic acid hybridization, presence or absence of marker gene functions and expression of the inserted sequences. Once a suitable host system and growth conditions are established, the recombinant molecules containing the glycosyltransferase gene can be introduced into the host cells via any procedure known in the art such as transformation, transfection, infection, electroporation, etc.

Once a source for the glycosyltransferases has been obtained, the source may be added directly to a reaction vessel for oligosaccharide synthesis. For example, host cells, such as *E. coli* cells, transformed with a polynucleotide that encode a crude, unpurified glycosyltransferase, can be added directly to a reaction vessel for use in the process of this invention. If the host cells express the glycosyltransferase into a culture medium, then the culture medium can be added to the reaction vessel. Additionally, the glycosyltransferase source can be homogenized and the homogenate added directly to a reaction vessel. If a purified glycosyltransferase is to be employed, the purified enzyme can be added directly to the reaction vessel. For example, if the glycosyltransferase source is homogenized, the glycosyltransferase can be purified from the homogenate by affinity chromatography using the acceptor moiety as the affinity ligand, using techniques known in the art.

In lieu of adding the unpurified or purified glycosyltransferase directly to the reaction vessel, the glycosyltransferase can instead be placed in a dialysis bag which can be inserted into a reaction vessel. The dialysis bag can be removed from the reaction ve ssel periodically and additional glycosyltransferases added when required. When the glycosyltransferase is contained in a dialysis bag, the acceptor moiety and sugar-nucleotides migrate into the bag and react with the glycosyltransferase to synthesize an oligosaccharide. When the synthesis of the oligosaccharide is completed, the oligosaccharide migrates out of the bag and into the surrounding medium.

The glycosyltransferases used in the present invention catalyze the transfer of sugar units from sugar-nucleotides to an acceptor moiety. The glycosyltransferases are preferably specific for a saccharide unit or at least some significant, active, or exposed portion thereof. Specificity is manifested for a glycosyltransferase by its tendency to bind with a particular sequenced portion of the acceptor moiety when placed in contact or close proximity therewith to effect the transfer of a particular sugar unit to the acceptor moiety.

A catalytic amount of a glycosyltransferase is employed in the process of the present invention. As used herein, a "catalytic amount" refers to the amount of glycosyltransferase that must be present to sufficiently catalyze the transfer of a sugar unit from a sugar-nucleotide to an acceptor moiety. The catalytic amount of glycosyltransferase employed in the process of the present invention can be determined by one of ordinary skill in the art through routine experimentation.

In the process of the present invention, an oligosaccharide can be synthesized by adding an acceptor moiety and a glycosyltransferase to a sugar-nucleotide to form a mixture and then maintaining the mixture under conditions and a period of time sufficient to allow for oligosaccharide formation. The conditions and time periods required for the formation of the oligosaccharide using the process of the present invention can be determined by one of ordinary skill in the art through routine experimentation. Generally, however, the mixture is incubated from about 4 to about 48 hours, at a temperature from about 4° to about 35° C. and at a pH from about 4 to about 9.0.

In the process of the present invention, an oligosaccharide can be synthesized using a crude, unpurified sugar-nucleotide produced from microorganisms and a crude, unpurified glycosyltransferase produced from host cells transformed with a polynucleotide that expresses a glycosyltransferase. For example, an oligosaccharide can be synthesized by adding an acceptor moiety and *E. coli* cells transformed with a polynucleotide that encodes a catalytic amount of a glycosyltransferase to a culture of *S. cerevisiae* that produce sugar-nucleotides to produce a mixture. The mixture is then maintained under conditions and for a period of time sufficient to allow for oligosaccharide formation.

Alternatively, an oligosaccharide can be synthesized by adding an acceptor moiety and a catalytic amount of a purified glycosyltransferase to a culture of microorganisms producing sugar-nucleotides to form a mixture and incubating the mixture under conditions and for a period of time sufficient to allow for oligosaccharide formation. Additionally, an oligosaccharide can be synthesized by adding an acceptor moiety and host cells transformed with a polynucleotide that encodes a catalytic amount of a glycosyltransferase to purified sugar-nucleotides to form a mixture and incubating the mixture under conditions and for a period of time sufficient to allow for oligosaccharide formation. The oligosaccharide formed by the process of this invention can serve as an acceptor moiety for additional oligosaccharide synthesis. If further synthesis is required, the oligosaccharide and a catalytic amount of a glycosyltransferase are added to sugar-nucleotides to form another mixture. The mixture is maintained under conditions and for a period of time sufficient for oligosaccharide formation. This process is repeated until a sufficient number of sugar units have been transferred to form the desired oligosaccharide.

The synthesis of oligosaccharides according to the process of the present invention may take place in one or a number of reaction vessels. If a single reaction vessel is used, the ingredients required for oligosaccharide synthesis may be added sequentially, one at a time. For example, the ingredients required for the formation of a microorganism culture that produces the sugar-nucleotides may be added first followed by the acceptor moiety and then host cells transformed with a polynucleotide that encodes a glycosyltransferase. Depending on the oligosaccharide to be synthesized, additional sugar-nucleotides and glycosyltransferases may be added to the reaction vessel if necessary. Alternatively, all of the ingredients required for the synthesis of a particular oligosaccharide may be added to the reaction vessel at the same time.

A number of reaction vessels may also be used for the synthesis of oligosaccharides. For example, the ingredients required for the formation of a microorganism culture producing sugar-nucleotides, an acceptor moiety and host cells transformed with a polynucleotide that encodes a glycosyltransferase may be added sequentially or at the same time into a reaction vessel. The resulting oligosaccharide is then removed from the reaction vessel to a second reaction vessel for additional synthesis. The oligosaccharide and host cells transformed with a polynucleotide that expresses a glycosyltransferase are added to sugar-nucleotides produced by a microorganism culture as needed until the desired oligosaccharide has been synthesized. Once the desired oligosaccharide has been synthesized, it is removed from the, reaction vessel and exposed to further processing such as centrifugation or decantation, ion exchange chromatography, tangential flow, filtration, reverse osmosis or spray drying and lyophilization to obtain a pure oligosaccharide.

The process of the present invention can be used to synthesize any oligosaccharide. For example, the process of the present invention can be used to synthesize oligosaccharides such as Lacto-N-neoTetraose (LNnT), lacto-N-fucopentaose (LNF-V), 2'-fucososyllactose (2'-FL), 3-fucosyllactose (3-FL), lacto-N-fucopentaose III (LNF-III), lacto-N-focopentaose II (LNF-II), difucosyllactose (DFL), lacto-N-fucopentaose (LNF-I) and Lacto-N-Tetraose (LNT).

The oligosaccharides produced, according to the process of this invention, find use in an exceedingly wide variety of applications and may be used in the same manner as saccharide compositions available from known sources. The present invention provides pharmaceuticals nutritional compositions and other oligosaccharide containing compositions prepared in accordance with the present invention.

The following examples illustrate preferred embodiments of the present invention and are not limiting of the claims and specification in any way.

EXAMPLE 1

Production of the Oligosaccharide LNnT in a Single Reaction Vessel UDP-GlcNAc Yeast Production System Dried yeast cells (*S. cerevisiae*) are fed 20 mM glucosamine, 170 mM $KH_2PO_4$, 5 mM $MgSO_4$, 70 mM fructose and 20 mM UMP. This yeast culture is incubated at room temperature. The yeast culture is monitored for the formation of the sugar-nucleotide UDP-GlcNAc. When the amount of UDP-GlcNAc produced is approximately 6.0 mM, the sugar-nucleotide yeast production system is added to a reaction vessel.

Trisaccharide—LNT-2 (GlcNAcβ1-3Galβ1-4Glc) Synthesis

*E. coli* cells expressing GlcNAc transferase (100 Units/Liter of Reaction) are homogenized, and, without any further purification, are added to the reaction vessel containing the UDP-GlcNAc production system. The GlcNAc transferase and UDP-GlcNAc yeast production system are incubated at room temperature until the residual UDP GlcNAc production is approximately 1.0 mM. 30 mM lactose is added to the reaction vessel as a substrate to produce material containing the trisaccharide intermediate LNT-2 (GlcNAcB1-3Galβ1-4Glc). The amount of LNT-2 containing material produced should be greater than 6 mM. *E. coli* whole cell homogenates may be substituted with *E. coli* intact cells +/− Triton X-100.

LNnT (Galβ1-4GlcNAcβ1-3Galβ1-4Glc) Synthesis

*E. coli* cells expressing Gal transferase (350 Units/Liter of Reaction) and fortuitously an epimerase are homogenized and added to the reaction vessel without any purification. The Gal transferase, the LNT-2 containing material and the UDP-Glc/yeast solution are incubated at room temperature until the residual production of the GlcNAcβ1-3Galβ1-4Glc is approximately 0.1 mM. The required UDP-Glc is produced by feeding dried yeast cells (*Candida famata*) 200–400 mM glucose (Glc), 180 mM $KH_2PO_4$, 12 mM $MgSO_4$ and 30–100 mM UMP. The yeast is incubated at room temperature for 10–48 hours and monitored for the production of UDP-Glc. When the amount of UDP-Glc produced exceeds 6 mM, the UDP-Glc yeast mixture is added to the reaction vessel to produce Lacto-N-neoTetraose (LNnT). The amount of LNnT containing material produced should be greater than 6 mM. The LNnT containing material is then removed from the reaction vessel and moved downstream for further processing such as by centrifugation or decantation, ion exchange chromatography, tangential flow filtration, reverse osmosis, spraying drying or lyophilization to obtain pure LNnT.

EXAMPLE 2

Production of LNnT in a Single Reaction Vessel Using a Two Yeast System LNT-2 (GlcNAβ1-3Galβ1-4Glc) Synthesis All of the reagents necessary for the synthesis of the intermediate LNT-2 are added simultaneously to one reaction vessel. More specifically, a mixture of dried *Candida famata* and *S. cerevisiae* are fed 20 mM glucosamine, 20 mM UMP, 170 mM $KH_2PO_4$, 5 mM $MgSO_4$, 70–175 mM fructose to produce the sugar-nucleotide UDP-GlcNAc. At the same time, 30 mM lactose and homogenized, unpurified *E. coli* cells expressing GlcNAc transferase (100 Units/Liter of Reaction Mix) are added. The entire reaction mixture is incubated at room temperature until the levels of LNT-2 containing material produced are greater than 6.0 mM.

LNnT (Galβ1-4GlcNAcβ1-3Galβ1-4Glc) Synthesis

Additional homogenized, unpurified *E. coli* cells expressing Gal transferase (350 units/Liter of Reaction) and an epimerase are added to the reaction vessel. More specifically, dried *Candida famata* are fed 200–400 mM glucose, 180 mM KH$_2$PO$_4$, 12 mM MgSO$_4$ and 20–100 mM UMP. The yeast is incubated at room temperature until the amount of UDP-Glc produced exceeds 6mM. The sugar-nucleotide yeast producing system is then added to the reaction vessel containing the LNT-2 containing material and the E. coli cells expressing Gal transferase to produce LNnT containing material. The LNnT containing material is then removed from the reaction vessel and moved downstream for further processing such as by centrifugation or decantation, ion exchange chromatography, tangential flow, filtration, reverse osmosis, spraying drying or lyophilization to obtain pure LNnT.

EXAMPLE 3
Production of LNnT In a Single Reaction Vessel Using a Two Yeast System by the Simultaneous Addition of Reagents All of the reagents necessary for the synthesis of LNnT are added simultaneously to one reaction vessel. More specifically, a mixture of dried Baker's yeast (*S. cerevisiae*) and *Candida famata* are fed 30 mM glucosamine, 40 mM UMP, 170 mM KH$_2$PO$_4$, 12 mM MgSO$_4$ and 200 mM maltose to produce the sugar-nucleotides UDP-GlcNAc and UDP-Glc. At the same time, 30 mM lactose, homogenized, unpurified *E. coli* cells expressing GlcNAc transferase (1900 U/L reaction) and homogenized, unpurified *E. coli* cells expressing Gal transferase (1000–2000 U/L reaction) are added to the same reaction vessel. The entire reaction mixture is incubated at room temperature and is allowed to proceed until the level of LNnT containing material is greater than 3 mM. The LNnT containing material is then removed from the reaction vessel and moved downstream for further processing such as by centrifugation or decantation, ion exchange chromatography, tangential flow, filtration, reverse osmosis, spraying drying or lyophilization to obtain pure LNnT.

EXAMPLE 4
Production of the Oligosaccharide LNnT in a Single Reaction Vessel Using a Two Yeast System by the Exogenous Addition of LNT-2.

All of the reagents necessary for the synthesis of LNnT are added simultaneously to one reaction vessel. More specifically a mixture of dried Baker's yeast and *Candida famata* are fed 30 mM glucosamine, 40 mM UMP, 170 mM KH$_2$PO$_4$, 12 mM MgSO$_4$ and 200 mM maltose to produce the sugar-nucleotide UDP-GlcNAc. At the same time, 30 mM lactose, 30 mM LNT-2, homogenized, unpurified *E. coli* cells expressing GlcNAc transferase (1900 Units/Liter of Reaction Mix) and homogenized, unpurified *E. coli* cells expressing Gal transferase (1000 Units/Liter of Reaction mix) are added to the reaction vessel. The entire reaction mixture is refrigerated or incubated at room temperature and is allowed to proceed until the levels of LNnT containing material reach at least 15 mM. The LNnT containing material is then removed from the reaction vessel and moved downstream for further processing such as by centrifugation or decantation, ion exchange chromatography, tangential flow, filtration, reverse osmosis or spraying drying and lyophilization to obtain pure LNnT.

EXAMPLE 5
Production of LNnT in a Single Reaction Vessel using a Single Yeast Production System All of the reagents necessary for the synthesis of LNnT are added simultaneously to one reaction vessel. More specifically, dried *Candida famata* are fed 30 mM glucosamine, 40 mM UMP, 170 mM KH$_2$PO$_4$, 12 mM MgSO$_4$ and 200 mM maltose to produce the sugar-nucleotides UDP-GlcNAc and UDP-Glc. At the same time, 30 mM lactose, intact *E. coli* cells expressing GlcNAc transferase (1900 Units/Liter of Reaction Mix) and intact *E. coli* cells expressing Gal transferase (2000 Units/Liter of Reaction mix) are also added to the reaction vessel. The entire reaction mixture is incubated at room temperature and is allowed to proceed until the levels of LNnT containing material reach at least 18 mM. The LNnT containing material is then removed from the reaction vessel and moved downstream for further processing such as by centrifugation or decantation, ion exchange chromatography, tangential flow, filtration, reverse osmosis, spraying drying or lyophilization to obtain pure LNnT.

EXAMPLE 6
Production of LNnT in a Single Reaction Vessel using a Single Yeast Production System and Orotate All of the reagents necessary for the synthesis of LNnT are added simultaneously to one reaction vessel. More specifically, dried *Candida famata* are fed 30 mM glucosamine, 40 mM orotate, 170 mM KH$_2$PO$_4$, 12 mM MgSO$_4$ and 200 mM glucose to produce the sugar-nucleotides UDP-GlcNAc and UDP-Glc. At the same time, 30 mM lactose, homogenized, unpurified *E. coli* cells expressing GlcNAc transferase (1900 Units/Liter of Reaction Mix) and homogenized, unpurified *E. coli* cells expressing Gal transferase (2000 Units/Liter of Reaction mix) are added to the reaction vessel. The entire reaction mixture is refrigerated or incubated at room temperature and is allowed to proceed until the levels of LNnT containing material reach at least 13 mM. The LNnT containing material is then removed from the reaction vessel and moved downstream for further processing such as by centrifugation or decantation, ion exchange chromatography, tangential flow, filtration, reverse osmosis or spraying drying and lyophilization to obtain pure LNnT.

EXAMPLE 7
Synthesis of LNnT in a Single Reaction Vessel Using Single Yeast Production System and LNT-2

A method that can be used for synthesizing LNnT using a single yeast production system and LNT-2 will now be described. All of the reagents necessary for the synthesis of LNnT can be added simultaneously to one reaction vessel. More specifically, dried *Candida famata* is fed 30 mM glucosamine, 40 mM UMP, 170 mM KH$_2$PO$_4$, 12 mM MgSO$_4$ and 200 mM maltose to produce the sugar-nucleotides UDP-GlcNAc and UDP-Glc. At the same time, 30 mM lactose, 30 mM LNT-2, homogenized, unpurified *E. coli* cells expressing GlcNAc transferase (1900 Units/Liter of Reaction Mix) and homogenized, unpurified *E. coli* cells expressing Gal transferase (2000 Units/Liter of Reaction mix) are added to the reaction vessel. The entire reaction mixture is incubated at room temperature and is allowed to proceed until the levels of LNnT containing material reach at least 18 mM. The LNnT containing material is then removed from the reaction vessel and moved downstream for further processing such as by centrifugation or decantation, ion exchange chromatography, tangential flow, filtration, reverse osmosis or spraying drying and lyophilization to obtain pure LNnT.

EXAMPLE 8
Production of the Oligosaccharide LNnT In Two Reaction Vessels Using a Two Yeast System
UDP-GlcNAc Production System Dried Baker's yeast are fed 20 mM glucosamine, 170 mM KH$_2$PO$_4$, 5 mM MgSO$_4$ and 70 mM fructose. 20 mM UMP is added to the yeast. The yeast are incubated at room temperature and monitored for the formation of the sugar-nucleotide UDP-GlcNAc. The yeast are incubated at room temperature until the amount of UDP-GlcNAc produced is approximately 6.0 mM. The sugar-nucleotide yeast producing system is added to a first reaction vessel.

Trisaccharide—LNT-2 (GlcNAcβ1-3Galβ1-4Glc) Synthesis $E.\ coli$ cells expressing GlcNAc transferase (350 units/Liter of Reaction Mix) are homogenized and, without any further purification, are added to the reaction vessel containing the UDP-GlcNAc yeast production system. The GlcNAc transferase and UDP-GlcNAc production system are incubated at room temperature until the residual UDP-GlcNAc production is less than 1.0 mM. Lactose is also added to the reaction vessel as a substrate to produce material containing the trisaccharide intermediate LNT-2 (GlcNAcβ-3Galβ1-4Glc). The amount of LNT-2 containing material produced should be greater than 6 mM. The LNT-2 containing material is removed from the first reaction vessel and transported to a second reaction vessel.

LNnT (Galβ1-4GlcNAcβ1-3Galβ1-4Glc) Synthesis

Additional homogenized and unpurified $E.\ coli$ cells expressing Gal transferase (350 units/Liter of Reaction) are added to the second reaction vessel containing the LNT-2 containing material and a source of UDP-Glucose. This material is incubated at room temperature until the residual production of the GlcNAcβ1-3Galβ1-4Glc is approximately 0.1 mM. The source of UDP-Glc is supplied by incubating $Candida\ famata$, 200–4100 mM glucose, 180 mM KPO$_4$, 12 mM MgSO$_4$ and 20–100 mM UMP. The microorganisms are incubated at room temperature until the amount of UDP-Glc produced is greater than 6 mM. The sugar-nucleotide yeast producing system is then added to the second reaction vessel containing the trisaccharide GlcNAcβ1-3Galβ1-4Glc and the Gal transferase to produce LNnT. The material containing the LNnT is then removed from the second reaction vessel and moved downstream for further processing such as by centrifugation or decantation, ion exchange chromatography, tangential flow, filtration, reverse osmosis or spraying drying and lyophilization to obtain pure LNnT.

EXAMPLE 9
Production of the Oligosaccharide LNnT in a Single Reaction Vessel Using a Single Yeast System Trisaccharide (LNT-2, GlcNAcβ1-3Galβ1-4Glc) Synthesis in the Absence of Added Nucleotide To dried $Candida\ famata$ cells, 50 mM glucosamine, 200 mM KH$_2$PO$_4$, 12 mM MgSO$_4$, 200 mM maltose, 100 mM lactose and homogenized, unpurified $E.\ coli$ cells expressing GlcNAc transferase (1200 Units/Liter reaction mix) are added. The entire mixture is incubated at room temperature with aeration. After 24 hours incubation, the reaction is supplemented with an additional 40 mM glucosamine and 200 mM maltose. The mixture is further incubated until greater than 55 mM LNT-2 is generated.

LNnT (Galβ1-4GlcNAcβ1-3Galβ1-4Glc) Synthesis

To the yeast/LNT-2 mix, air dried $Candida\ famata$, 400 mM glucose (or galactose), 180 mM KH$_2$PO$_4$, 12 mM MgSO$_4$ and homogenized, unpurified $E.\ coli$ cells (expressing Gal transferase (1000 Units/Liter reaction mix) are added. The reaction is incubated at room temperature with aeration until at least 50 mM LNnT is produced. The LNnT containing material is then removed from the reaction vessel and moved downstream for further processing such as by centrifugation or decantation, ion exchange chromatography, tangential flow filtration, reverse osmosis, spray drying or lyophilization to obtain pure LNnT.

EXAMPLE 10
Production of the Oligosaccharide LNnT in Two Reaction Vessels Using a Single Yeast System Trisaccharide (LNT-2, GlcNAcβ1-3Galβ1-4Glc) Synthesis in the Absence of Added Nucleotide To dried $Candida\ famata$ cells, 50 mM glucosamine, 200 mM KH$_2$PO$_4$, 12 mM MgSO$_4$, 200 mM maltose, 100 mM lactose and homogenized, unpurified $E.\ coli$ cells expressing GlcNAc transferase (1200 Units/Liter reaction mix) are added. The entire mixture is incubated at room temperature with aeration. After 24 hours incubation, the reaction is supplemented with an additional 40 mM glucosamine and 200 mM maltose. The mixture is further incubated until greater than 55 mM LNT-2 is generated. The LNT-2 i s semi-purified by a combination of methods including centrifugation, ion exchange chromatography, tangential flow filtration and reverse osmosis. This LNT-2 material is transferred to a second reactor.

LNnT (Galβ1-4GlcNAcβ1-3Galβ1-4Glc) Synthesis

In the second reactor, air dried $Candida\ famata$, 400 mM glucose (or galactose), 180 mM KH$_2$PO$_4$, 12 mM MgSO$_4$, 100 mM UMP, the LNT-2 material and homogenized, unpurified $E.\ coli$ cells expressing Gal transferase (1000 Units/Liter reaction mix) are added. The reaction is incubated at room temperature with aeration until at least 50 mM LNnT is produced. The LNnT containing material is then removed from the reaction vessel and moved downstream for further processing such as by centrifugation or decantation, ion exchange chromatography, tangential flow filtration, reverse osmosis, spray drying or lyophilization to obtain pure LNnT.

EXAMPLE 11
Production of the Oligosaccharide LNnT in a Single Reaction Vessel Using a Single Yeast System in the Absence of Added Nucleotide.

All of the reagents necessary for the synthesis of LNnT are added simultaneously to one reaction vessel. More specifically, dried $Candida\ famata$ are fed 50 mM glucosamine, 200 mM KH$_2$PO$_4$, 12 mM MgSO$_4$, 100 mM maltose to produce the sugar-nucleotides UDP-GlcNAc and UDP-Glc. At the same time, 100 mM lactose and homogenized, unpurified $E.\ coli$ cells expressing GlcNAc Transferase (1500 Units/Liter reaction mix) are added to the reaction vessel. The entire mixture is incubated at room temperature with aeration. After 18 hours, the reaction is supplemented with an additional 50 mM glucosamine and 100 mM maltose. After 23 hours, 200 mM galactose and homogenized, unpurified $E.\ coli$ cells expressing Gal transferase (1000 Units/Liter reaction mix) are added to the reaction vessel. The reaction is allowed to proceed until the levels of LNnT reach at least 40 mM (approximately 46 hours). The LNnT containing material is then removed from the reaction vessel and moved downstream for further processing such as by centrifugation or decantation, ion exchange chromatography, tangential flow filtration, reverse osmosis, spray drying or lyophilization to obtain pure LNnT.

EXAMPLE 12
Production of the Oligosaccharide Lacto-N-fucopentaose III (LNF-III) in a Single Reaction Vessel by the Addition of LNnT.

A method that can be used for synthesizing the oligosaccharide lacto-N-fucopentaose (LNF-III) will now be described. More specifically, dried $Torulopsis\ candida$ are fed 30 mM fucose, 40 mM GMP and 30 mM fructose to produce the sugar-nucleotides GMP-fucose. At the same time, 20 mM LNnT-2 and homogenized, unpurified $E.\ coli$ cells expressing α-1,3 fucosyltransferase (1900 Units/Liter of Reaction Mix) are homogenized and added without any purification to the reaction vessel. The entire reaction mixture is incubated at room temperature and is allowed to proceed until the levels of LNF-III containing material reach at least 5 mM. The LNF-III containing material is removed from the reaction vessel and moved downstream for further processing such as centrifugation or decantation, ion exchange chromatography, tangential flow, filtration, reverse osmosis, spraying drying or lyophilization to obtain pure LNF-III.

What is claimed is:

1. A process of synthesizing an oligosaccharide comprising the steps of:
   (a) adding an isolated exogenous acceptor moiety and a catalytic amount of an isolated exogenous glycosyltransferase to a microorganism culture that produces a sugar-nucleotide having a sugar unit to produce a mixture wherein said exogenous glycosyltransferase catalyzes the transfer of the sugar unit from the sugar-nucleotide to said exogenous acceptor moiety in the mixture; and
   (b) maintaining the mixture under conditions and for a period of time sufficient for oligosaccharide formation.

2. The process of claim 1 wherein the acceptor moiety is a monosaccharide.

3. The process of claim 1 wherein the acceptor moiety is a di, tri- or oligosaccharide.

4. The process of claim 1 wherein the glycosyltransferase is produced by host cells transformed with a polynucleotide that encodes the glycosyltransferase.

5. The process of claim 4 wherein the transformed cells are added to the microorganism culture.

6. The process of claim 4 wherein the glycosyltransferase is contained in a culture medium of the host cells.

7. The process of claim 1 wherein the microorganism is from the genus Saccharomyces, Zygosaccharomyces, Torulopsis, Candida, Cryopcoccus, Brettanomyces, Mucor, Hansenula, or Debaryomyces.

8. The process of claim 7 wherein the microorganism is *Saccharomyces cerevisiae, Candida famata,* or *Zygosaccharomyces rouxii.*

9. The process of claim 1 wherein the microorganism culture further comprises an epimerase.

10. The process of claim 1 wherein the saccharide nucleotides are UDP-glucose, UDP-N-acetylgalactosamine, UDP-Galactose, UDP-N-acetylgalactosamine, GDP-Mannose, GDP-fucose or CMP-N-acetylneuraminic acid.

11. The process of claim 1 wherein the mixture is maintained for about 4 to about 48 hours, at a temperature from about 4° C. to about 35° C. and at a pH from about 4 to about 9.

12. The process of claim 1 wherein the acceptor moiety and the glycosyltransferase are added at the same time.

13. The process of claim 1 wherein the acceptor moiety is added before the glycosyltransferase.

14. A process of synthesizing an oligosaccharide comprising the step of:
   a) adding an acceptor moiety and host cells transformed with a polynucleotide that encodes a catalytic amount of a glycosyltransferase to sugar-nucleotides having a sugar unit to produce a mixture wherein the glycosyltransferase catalyzes the transfer of the sugar unit of the sugar-nucleotide to the acceptor moiety in the mixture; and
   b) maintaining the mixture under conditions and for a period of time sufficient for oligosaccharide formation.

15. The process of claim 14 wherein the acceptor moiety is a monosaccharide.

16. The process of claim 14 wherein the acceptor moiety is a di, tri- or oligosaccharide.

17. The process of claim 14 wherein the saccharide nucleotides are UDP-glucose, UDP-N-acetylgalactosamine, UDP-Galactose, UDP-N-acetylgalactosamine, GDP-Mannose, GDP-fucose or CMP-N-acetylneuraminic acid.

18. The process of claim 14 wherein the sugar-nucleotide is contained in a culture of microorganisms.

19. The process of claim 18 wherein the microorganism is from the genus Saccharomyces, Zygosaccharomyces, Torulopsis, Candida, Cryopcoccus, Brettanomyces, Mucor, Hansenula, or Debaryomyces.

20. The process of claim 14 wherein the mixture is maintained from about 4 to about 48 hours, at a temperature from about 4° C. to about 35° C. and at a pH from about 4 to about 9.

21. The process of claim 14 wherein the acceptor molecule and the host cells are added at the same time to the sugar-nucleotide.

22. The process of claim 14 wherein the acceptor moiety is added to the sugar-nucleotide before the host cells.

* * * * *